(12) United States Patent
Iyoha et al.

(10) Patent No.: US 9,314,428 B2
(45) Date of Patent: Apr. 19, 2016

(54) ORAL COMPOSITION COMPRISING A COOLING AGENT

(75) Inventors: Kingsley Iyoha, Manchester (GB); Neil Campbell Muir, Hull (GB); Robert Rhoades, Kimberley (GB); Alden Rodwell, Hull (GB); David Michael Thurgood, Long Eaton (GB)

(73) Assignee: RECKITT BENCKISER HEALTHCARE (UK) LIMITED, Slough, Berkshire (GB)

( * ) Notice: Subject to any disclaimer, the term of this patent is extended or adjusted under 35 U.S.C. 154(b) by 600 days.

(21) Appl. No.: 12/738,178

(22) PCT Filed: Oct. 17, 2008

(86) PCT No.: PCT/GB2008/003543
§ 371 (c)(1), (2), (4) Date: May 17, 2010

(87) PCT Pub. No.: WO2009/050490
PCT Pub. Date: Apr. 23, 2009

(65) Prior Publication Data
US 2010/0216830 A1 Aug. 26, 2010

(30) Foreign Application Priority Data
Oct. 19, 2007 (GB) .................................. 0720425.8

(51) Int. Cl.
| | |
|---|---|
| *A01N 43/42* | (2006.01) |
| *A61K 31/44* | (2006.01) |
| *A61K 31/045* | (2006.01) |
| *A61K 9/00* | (2006.01) |
| *A23G 4/06* | (2006.01) |
| *A61K 8/02* | (2006.01) |
| *A61K 8/34* | (2006.01) |
| *A61K 31/00* | (2006.01) |
| *A61Q 11/00* | (2006.01) |
| *A61K 9/68* | (2006.01) |

(52) U.S. Cl.
CPC ................ *A61K 9/0056* (2013.01); *A23G 4/06* (2013.01); *A61K 8/0216* (2013.01); *A61K 8/345* (2013.01); *A61K 31/00* (2013.01); *A61Q 11/00* (2013.01); *A61K 9/006* (2013.01); *A61K 9/0058* (2013.01); *A61K 2800/244* (2013.01)

(58) Field of Classification Search
USPC ................................... 514/289, 738, 733, 568
See application file for complete search history.

(56) References Cited

U.S. PATENT DOCUMENTS

| | | | |
|---|---|---|---|
| 3,123,528 A * | 3/1964 | Fenton .......................... | 514/730 |
| 2007/0081949 A1 * | 4/2007 | Dam et al. ...................... | 424/48 |
| 2009/0081294 A1 * | 3/2009 | Gin et al. ...................... | 424/486 |

FOREIGN PATENT DOCUMENTS

WO    WO 2005067906 A2 *    7/2005

* cited by examiner

*Primary Examiner* — Shirley V Gembeh
(74) *Attorney, Agent, or Firm* — Troutman Sanders LLP; Ryan A. Schneider; Troy S. Kleckley

(57) ABSTRACT

The present invention relates to a formulation comprising an endothermic cooling agent selected from the group consisting of xylitol, sorbitol, mannitol and erythritol having a heat of enthalpy between −10 cal/g and −100 cal/g, and one or more active agents wherein the endothermic agent is present in the formulation at an amount less than 10% w/w.

8 Claims, No Drawings

ORAL COMPOSITION COMPRISING A COOLING AGENT

CROSS-REFERENCES TO RELATED APPLICATIONS

This application is a US National Stage of International Application No. PCT/GB2008/003543, filed 17 Oct. 2008, which claims the benefit of GB 0720425.8, filed 19 Oct. 2007.

FIELD OF THE INVENTION

The present invention relates to an oral composition which contains a cooling agent. In particular, the present invention relates to medicament containing a cooling agent. More particularly, the present invention relates to a medicament for treating sore throats which contains xylitol.

BACKGROUND OF THE INVENTION

Cooling agents have been used in a number of different formulations, such as hard confectionary products or oral gums, to provide a pleasant taste and a cooling sensation. For example, compounds such as menthol or peppermint oil have been used in either as part of the formulation or as part of a coating in order to provide the user with a cooling sensation.

Cooling agents have also been used in pharmaceutical formulations to enhance the physiological and/or perceived benefits, such as speed or duration of relief. Such agents are commonly used in non-prescription cough medicines.

Sore throats are generally treated using pharmaceutical lozenges containing a therapeutically effective amount of an active compound. Suitably, the lozenge is sucked by a patient in need of such treatment and the active is released in the oral cavity and delivered to the surface of the sore throat (i.e. mucous membrane).

Some of the actives which are used to relieve the symptoms associated with a sore throat can cause an unpleasant burning sensation at the back of the mouth when retained in the mouth, e.g a non-steroidal anti-inflammatory drug (NSAID). This is unacceptable to the patient being treated. Consequently, pharmaceutical lozenges containing actives such as an NSAID have been devised where the lozenge formed therefrom relieves the symptoms of a sore throat but the patient does not experience an unacceptable burning sensation.

Cooling agents have also been used with sweeteners in liquid cough-treatment compositions. The limited portability of liquids limits the use of coolants in liquid compositions, and some high-intensity sweeteners, such as aspartame, are subject to degradation when heated.

In addition, the cooling agent itself can result in a burning effect if used at too high a level in the composition.

The cooling effect or sensation of cooling in the mouth is usually achieved using a polyol. The effect is caused by the negative heat of dissolution of such polyols in water, and is also linked to their rate of dissolution. Crystalline xylitol is in this respect particularly effective since it confers the most intense cooling sensation. Sorbitol and erythritol have slightly lower cooling effects than xylitol.

Xylitol, also called wood sugar or birch sugar, is a five-carbon sugar alcohol that can be used as a sugar substitute. It is derived from various types of cellulose products, such as wood, straw, cane pulp, seed hulls and shells. Xylitol is an odourless, sweet tasting granular solid (comprising crystalline, equi-dimensional particles). Xylitol has a sweetness level equivalent to sugar. The combination of a relatively large negative heat of solution and high solubility means that xylitol provides cooling sensation in the mouth that is said to be refreshing.

Sorbitol is a popular bulk sweetener found in numerous food products. In addition to providing sweetness, it is an excellent humectant and texturizing agent. Mannitol is a monosaccharide polyol. Both sorbitol and mannitol are generally stable and chemically unreactive.

The main disadvantage of xylitol is that it is an expensive ingredient. In addition, it is generally understood that a cooling effect will only be obtained when using crystalline xylitol. Accordingly, xylitol is often replaced with a less expensive sugarless polyol, such as sorbitol.

The use of sorbitol is well-known and described. There are numerous patent publications disclosing such a use, for example GB 2 115 672, U.S. Pat. No. 4,317,838 and U.S. Pat. No. 4,753,790.

BRIEF SUMMARY OF THE INVENTION

It would be desirable to be able to use xylitol in a lower amount. However, it is thought that the presence of a small quantity of xylitol in a formulation would not produce a significant sensation of coolness.

DETAILED DESCRIPTION OF PREFERRED EMBODIMENTS

According to a first aspect of the present invention there is provided a formulation comprising an endothermic cooling agent having a heat of enthalpy between −10 cal/g and −100 cal/g, and one or more active agents wherein the endothermic agent is present in the formulation at an amount less than 10% w/w.

The endothermic cooling agent can have a heat of enthalpy in the range −10 cal/g to −50 cal/g. A more preferred endothermic cooling agent can have a heat of enthalpy in the range −20 cal/g to −35 cal/g.

The endothermic cooling agent can be present in the medicament at an amount in the range of from 1-5%. A preferred range is from 1-3%.

The endothermic cooling agent can be a polyol, preferably selected from the group consisting of xylitol, sorbitol, mannitol and erythritol.

The active agent is preferably selected from the group comprising, but not limited to, 2,4-dichlorobenzyl alcohol (DCBA), amyl metacresol (AMC), hexylresorcinol, flurbiprofen, lidocaine, benzocaine, cetylpyridinium chloride, dequalinium chloride, menthol, ambroxol hydrochloride, dextromethorphan hydrobromide and guaifenesin.

The formulation can be in any suitable form including lozenge, gel, spray, capsule, pastille, gum or tablet.

The agent can form part of a coating when the formulation is in a form which is suitable for coating.

Preferably the formulation does not contain a high intensity sweetener.

The formulation may contain additional excipients as required. Typical excipients include, but are not limited to, acidity regulators, opacifiers, colouring agents, stabilising agents, buffering agents, sweeteners, flavourings and preservatives.

According to a second aspect of the present invention there is provided the use of an endothermic cooling agent having a heat of enthalpy between −10 cal/g and −100 cal/g in a medicament wherein the endothermic agent is present in the medicament at an amount less than 10% w/w.

The endothermic cooling agent can have a heat of enthalpy in the range −10 cal/g to −50 cal/g. A more preferred endothermic cooling agent can have a heat of enthalpy in the range −20 cal/g to −35 cal/g.

The endothermic cooling agent can be present in the medicament at an amount in the range of from 1-5%. A preferred range is from 1-3%.

The endothermic cooling agent can be a polyol, preferably selected from the group consisting of xylitol, sorbitol, mannitol and erythritol The active agent is preferably selected from the group comprising 2,4-dichlorobenzyl alcohol (DCBA), amyl metacresol (AMC), hexylresorcinol, flurbiprofen, lidocaine, benzocaine, cetylpyridinium chloride, dequalinium chloride, menthol, ambroxol hydrochloride, dextromethorphan hydrobromide and guaifenesin.

The medicament can be in any suitable form including lozenge, gel, spray, capsule, pastille or gum.

The agent may form part of a coating when the medicament is in a form which is suitable for coating.

Preferably the medicament does not contain a high intensity sweetener.

The medicament may contain additional excipients as required. Typical excipients include, but are not limited to, acidity regulators, opacifiers, colouring agents, stabilising agents, buffering agents, sweeteners, flavourings and preservatives.

According to a third aspect of the present invention there is provided a use of an endothermic cooling agent for the preparation of the medicament of the second aspect of the present invention for the treatment of a sore throat.

The preferred form of the present invention is a solid form, such as a lozenge, which can be sucked or chewed thus releasing the endothermic cooling agent in the mouth of a patient. The cooling agent can then pass over the surface of the throat and provide relief to a patient.

In the context of the present invention the term 'endothermic cooling agent' as use herein refers to a compound, such as xylitol, which actually cools the body locally as a result of having a significant negative heat of dissolution. In contrast compounds such as menthol are generally referred to as a 'physiological cooling agent' on the basis that they cause the body to perceive a low temperature even though this is usually erroneous.

For the avoidance of doubt the formulations as defined in the first aspect of the invention includes confectionery products, food supplements and foodstuffs, nutraceuticals, medicinal and non-medicinal products wherein non-medicinal products includes products which would not be considered as confectionery products, e.g. non-prescription lozenges for the treatment of conditions such as sore throats.

An example embodiment of the present invention will now be described.

EXAMPLE FORMULATION

| Standard Name | mg | % |
| --- | --- | --- |
| Sucrose/Glucose Syrup | 2481.06 | 95.42% |
| Xylitol | 40 | 1.54% |
| Flavouring | 18 | 0.70% |
| Levomethol Ph Eur Natural | 8 | 0.31% |
| 2,4-Dichlorobenzyl Alcohol | 1.2 | 0.05% |
| Amylmetacresol BP | 0.615 | 0.02% |
| Eucalyptus Oil Ph Eur | 0.5 | 0.02% |
| Total (incl. theoretical 2% moisture) | 2600 | |

The lozenges are prepared using a process based on mixing constant streams of ingredients, which is conventional for the high-speed manufacture of high-boiled lozenge products. The liquid sucrose and the liquid glucose are mixed to form a syrup, which is fed into a holding vessel. The syrup is then pumped from the holding vessel into the cooker system, where the water content is reduced which results in the formation of the lozenge base. The lozenge base is drawn from the cooker in a continuous stream and fed into the mixing chamber; lozenge essence (containing active ingredients and flavour) is added with crystalline xylitol at a rate proportional to the flow of the lozenge base. This forms the lozenge mass.

The lozenge mass then flows continuously from the mixing chamber onto a tempering belt where it is cooled prior to lozenge formation and further cooling.

Alternative dosage forms, e.g. a chewable solid dosage form, can be produced using methods well-known and described to the man skilled in the art.

To demonstrate a localised physical cooling of lozenges containing xylitol, various samples of lozenges were prepared in the laboratory.

The following lozenges were made:
1. Plain Sugar-glucose lozenges
2. Sugar-glucose lozenges containing levomenthol (8 mg per 2.6 g lozenge)
3. Sugar-glucose lozenges containing Xylitol (40 mg per 2.6 g lozenge 1.5% w/w)
4. Sugar-glucose lozenges containing Xylitol (40 mg per 2.6 g lozenge 4.6% w/w)

The plain sugar-glucose lozenges were included in the experiment as a reference point for this cooling. As xylitol provides cooling via a different mechanism to menthol, samples containing menthol were also included in this experiment to highlight this difference.

The samples of lozenges identified above (i.e. 1-4) were tasted by a number of individuals.

The participants were asked to indicate whether they got a sense of cooling on the surface of the lozenge when in contact with any part of the mouth. The participants were also asked to rank from 1 to 4 (most cool-4 least cool) the surface cooling of the lozenges.

The table below indicates how the participants scored the samples in terms service coolness. A score of 1 is considered the most cool, whereas a score 4 is the least cool.

| Participant | Lozenge 1 | Lozenge 2 | Lozenge 3 | Lozenge 4 |
| --- | --- | --- | --- | --- |
| 1 | 4 | 3 | 2 | 1 |
| 2 | 4 | 3 | 2 | 1 |
| 3 | 4 | 3 | 1 | 2 |
| 4 | 4 | 3 | 2 | 1 |
| 5 | 4 | 3 | 2 | 1 |

KEY
Lozenge 1 - Plain Sugar-glucose lozenges
Lozenge 2 - Sugar-glucose lozenges containing levomenthol
Lozenge 3 - Sugar-glucose lozenges containing Xylitol (40 mg per 2.6 g lozenge 1.5% w/w)
Lozenge 4 - Sugar-glucose lozenges containing Xylitol (120 mg per 2.6 g lozenge 4.6% w/w)

Each participants perceived surface cooling to be exhibited most in the lozenges containing xylitol. The majority of participants were able to identify the lozenge with the higher quantity of xylitol as being the most cooling.

Accordingly the presence of xylitol in a lozenge at low concentrations (1.5% w/w-4.6% w/w) results in the lozenge exhibiting unexpectedly strong cooling properties.

Generally, any polyol may be used in the present invention as they have a sweet taste and can be used to provide a cooling effect in the mouth. Commonly-used polyols include xylitol, mannitol, sorbitol and erythritol. However, the man skilled in the art will recognize that a variety of polyols and combinations of polyols may be used.

In an alternative embodiment the actives, components DCBA and AMC, can be replaced by flurbiprofen, hexylresorcinol, lidocaine, benzocaine, cetylpyridinium chloride, dequalinium chloride, menthol, ambroxol hydrochloride, dextromethorphan hydrobromide or guaifenesin.

Further modifications and improvements can be incorporated without departing from the scope of the invention disclosed herein.

What is claimed is:

1. A formulation comprising:
   an endothermic cooling agent having a heat of enthalpy between −10 cal/g and −100 cal/g; and one or more active agents;
   wherein the endothermic cooling agent is present in the formulation at an amount less than 10% w/w; wherein the endothermic cooling agent is selected from the group consisting of xylitol, sorbitol, mannitol and erythritol;
   wherein the active agent comprises menthol and 2,4-dichlorobenzyl alcohol and amyl metacresol in a weight ratio of about 15.2:2.5:1; and
   wherein the formulation is used for the treatment of a sore throat.

2. The formulation as claimed in claim 1 wherein the endothermic cooling agent has a heat of enthalpy in the range −10 cal/g to −50 cal/g.

3. The formulation as claimed in claim 2 wherein the endothermic cooling agent has a heat of enthalpy in the range −20 cal/g to −35 cal/g.

4. The formulation as claimed in claim 1 wherein the endothermic cooling agent is present in the formulation at an amount in the range of 1-5%.

5. The formulation as claimed in claim 4 wherein the range of the endothermic cooling agent is 13%.

6. The formulation as claimed in claim 1 wherein the formulation is selected from the group consisting of a lozenge, gel, spray, capsule, pastille, gum and tablet.

7. The formulation as claimed in claim 1 wherein said formulation contains one or more additional excipients selected from the group consisting of acidity regulators, opacifiers, colouring agents, stabilising agents, buffering agents, sweeteners, flavourings and preservatives.

8. An oral composition comprising the formulation of claim 1.

* * * * *